(12) United States Patent
Kinsella et al.

(10) Patent No.: US 6,500,859 B2
(45) Date of Patent: Dec. 31, 2002

(54) METHOD FOR TREATING ATHEROSCLEROSIS OR RESTENOSIS USING MICROTUBULE STABILIZING AGENT

(75) Inventors: James L. Kinsella, Baltimore, MD (US); Steven J. Sollott, Baltimore, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/121,500

(22) Filed: Apr. 11, 2002

(65) Prior Publication Data

US 2002/0143048 A1 Oct. 3, 2002

Related U.S. Application Data

(63) Continuation of application No. 08/821,906, filed on Mar. 21, 1997, which is a continuation of application No. 08/633,185, filed on Apr. 18, 1996, now Pat. No. 5,616,608, which is a continuation of application No. 08/099,067, filed on Jul. 29, 1993, now abandoned.

(51) Int. Cl.$^7$ ................... A61K 31/337; C07D 308/14
(52) U.S. Cl. ................... 514/449; 549/510; 549/511; 514/824
(58) Field of Search .................. 514/449; 549/510, 549/511

(56) References Cited

U.S. PATENT DOCUMENTS

| | | | |
|---|---|---|---|
| 4,939,168 A | 7/1990 | Gunasekera et al. | 514/459 |
| 5,010,099 A | 4/1991 | Gunasekera et al. | 514/459 |
| 5,157,049 A | 10/1992 | Haugwitz et al. | 514/449 |
| 5,223,269 A | 6/1993 | Liepens | 424/600 |
| 5,580,898 A | 12/1996 | Trojanowski et al. | 514/449 |
| 5,616,608 A | 4/1997 | Kinsella et al. | 514/449 |
| 5,667,764 A | 9/1997 | Kopia et al. | 424/1.45 |
| 5,716,981 A | 2/1998 | Hunter et al. | 514/449 |
| 5,733,925 A | 3/1998 | Kunz et al. | 514/449 |
| 5,770,609 A | 6/1998 | Grainger et al. | 514/319 |
| 5,811,447 A | 9/1998 | Kunz et al. | 514/411 |
| 5,886,026 A | 3/1999 | Hunter et al. | 514/449 |
| 5,981,568 A | 11/1999 | Kunz et al. | 514/411 |
| 6,262,079 B1 | 7/2001 | Grainger et al. | 514/319 |
| 6,268,390 B1 | 7/2001 | Kunz | 514/411 |

FOREIGN PATENT DOCUMENTS

| | | |
|---|---|---|
| WO | WO 9311120 | 6/1993 |
| WO | WO 95/03036 | 2/1995 |
| WO | WO 95/03795 | 9/1995 |

OTHER PUBLICATIONS

Bard et al., Normolipemic Activities of Acrylophenone Derivatives with Antimicrotubular Properties; *Meth. and Find. Clin. Pharmacol.*; 7:183–187 (1985).

Bollag, D.M. et al., Epothilones, a New Class of Microtubule–Stabilizing Agents with a Taxol–like Mechanism of Action; *Cancer Research*; 55:2325–2333 (1995).

Chaldakov G. N., Antitubulins—A New Therapeutic Approach for Atherosclerosis?; *Atherosclerosis*; 44:385–390 (1982).

Currier, Jesse V. et al.; Colchicine Inhibits Restenosis After Iliac Angioplasty in the Atherosclerotic Rabbit; *Supplement II Circulation*; 80:II–66 (1989).

Ferns, Gordon A.A. et al.; Inhibition of Neointimal Smooth Muscle Accumulation After Angioplasty by an Antibody to PDGF; *Science*; 253:1129–1132 (1991).

Godeau, G. et al.; Effect of Colchicine on Atherosclerosis–III. Study of Dermal Elastic Fibers By Quantitive Histochemistry, Automated Image Analysis; *Clinical Physiology and Biochem.*; 3:234–239 (1985).

Harris, P. et al.; Conditions for Assembly of Tubulin–based Structures in Unfertilized Sea Urchin Eggs; *J. of Cell Science*; 102:557–567 (1992).

Hollander, Wm., et al.; Effects of Anticalcifying and Antifibrobrotic Drugs on Pre–Established Atherosclerosis in the Rabbit; *Atherosclerosis*; 33:111–123 (1979).

Hwang, B.D. et al.: (Computer database abstract of) Promotion of Microtubule Assembly in Vitro by a Novel 35–kDa Protein Purified From Human Term Placenta; *Biochem. Biophys. Res. Commun.*; 208(3):1174–1180 (1995).

International Search Report of PCT Application WO85/03036 (International Application No. PCT/CA94/00373).

International Search Report of PCT Application WO95/03795 (International Application No. PCT/CA94/08578).

Katsuda, S. et al., Inhibitory Effect of Dimethyl Sulfoxide on the Proliferation of Cultured Arterial Smooth Muscle Cells: Relationship to the Cytoplasmic Microtubules; *Experimental and Molecular Pathology* 48:48–58 (1988).

Lacy, P.E. et al.: (Computer database abstract of) Cinemicrographic Studies on Beta Granule Movement in Monolayer Culture of Islet Cells; *Lab. Invest.*; 33(5):570–576 (1975).

(List continued on next page.)

*Primary Examiner*—Ba K. Trinh
(74) *Attorney, Agent, or Firm*—Klarquist Sparkman, LLP

(57) ABSTRACT

The present invention is a method of preventing or reducing atherosclerosis or restenosis, and a pharmaceutical preparation used therefor. In particular, it is a method of preventing or reducing atherosclerosis or restenosis after arterial injury by treatment with a low dose of a microtubule stabilizing agent such as taxol or a water soluble taxol derivative. The low dose used in the present invention prevents artery blockage while minimizing any negative side effects associated with the drug.

4 Claims, 5 Drawing Sheets

OTHER PUBLICATIONS

Lamprecht, J. et al.; Derangement of Microtubule Arrays in Interphase and Mitotic PtK2 Cells Treated with Deuterium Oxide (Heavy Water); *J. Cell Sci.*; 98:463–473 (1991).

Leff, D.N.; Taxol–like Activity Starts Epothilone on Fast Track to Anticancer Drug Discovery; *Bioworld Today*; 8(94);1–6 (1997).

Lövquist et al.; Pathophysiological Mechanism for Restenosis Following Coronary Angioplasty: Possible Preventive Alternatives; *J. of Int. Med.*, 233:215–226 (1993).

Mooberry, S.L. et al.; (Computer database abstract of) Tubercidin Stablizes Microtubules Against Vinblastine–Induced Depolymerization, A Taxol–Like Effect; *Cancer Lett.*, 96(2):261–266 (1995).

*The Merck Index*; Merck Co., Inc.: 9049:1435 (1989).

Muller, David W.M. et al.; Colchicine and Antineoplastic Therapy for the Prevention of Restenosis After Percutaneous Coronary Interventions; *J. of the Amer. Coll. of Cardiol.*; 17(6):126B–131B (1991).

O'Keefe, Jr., James H., et al.; Ineffectiveness of Colchicine for the Prevention of Restenosis After Coronary Angioplasty; *J. Amer. Coll. of Cardiol.*; 19(7):1597–1600 (1992).

Ross, R. The Pathogenesis of Atherosclerosis: A Perspective for the 1990's; *Nature*362:801–819 (1991).

Rowinsky Erik E. et al.; Taxol: A Novel Investigational Antimicrotubule Agent;*J. of the Nat. Cancer Inst.*; 82:1247–1259 (1990).

Schiff, P.B. et al.; Promotion of Microtubule Assembly In Vitro By Taxol; *Nature*; 277:665–667 (1979).

Schiff, P.B. et al.; Taxol Assemblies Tubulin in the Absence of Exogenous Guanosine 5'–Triphosphate or Microtubule–Associated Proteins; *Biochemistry*; 20:3247–3252 (1981).

Service, R.; Tumor–killer Made; How Does It Work?; *Science*; 247:2009 (1996).

Seybold, J. et al.; (Computer database abstract of) Studies on Intracellular Transport of Secretory Proteins in the Rat Exocrine Pancreas. II. Inhibition of Antimicrotubular Agents; *Virchows Arch. A. Pathol. Anat. Histol.*; 28(4):309–327 (1975).

Sollot S.J. et al.: Taxol Inhibits Neointimal Smooth Muscle Cell Accumulation After Angioplasty in the Rat; *J. Clin. Invest.*; 95(4):1869–1876 (1995).

Ter Haar, E. et al.; Discodermolide, A Cytotoxic Marine Agent That Stabilizes Microtubules More Potently than Taxol; *Biochemistry*; 35:243–250 (1996).

Vasdev, S. et al.; Deuterium Oxide Normalizes Blood Pressure and Elevated Cytosolic Calcium in Rats with Ethanol–Induced Hypertension; *Can. J. Cardiol.*; 9(9):802–808 (1993).

METHOD FOR TREATING ATHEROSCLEROSIS OR RESTENOSIS USING MICROTUBULE STABILIZING AGENT

PRIORITY CLAIM

This is a continuation of U.S. application Ser. No. 08/821,906 filed Mar. 21, 1997, allowed which is a continuation of U.S. application Ser. No. 08/633,185 filed Apr. 18, 1996 (issued as U.S. Pat. No. 5,616,608), which is a continuation of U.S. application Ser. No. 08/099,067 filed Jul. 29, 1993, abandoned.

FIELD OF THE INVENTION

The present invention relates to a method of treating patients at risk of developing atherosclerosis or restenosis.

More particularly, the invention relates to treatment of these patients with a low dose taxol solution to prevent or reduce the development of atherosclerosis or restenosis.

BACKGROUND OF THE INVENTION

Vascular disease is the leading cause of death and disability in the developed world, particularly afflicting the elderly. In the United States alone, despite recent encouraging declines, cardiovascular disease is still responsible for almost one million fatalities each year and more than one half of all deaths; almost 5 million persons afflicted with cardiovascular disease are hospitalized each year. The cost of this disease in terms of human suffering and of material resources is almost incalculable.

Atherosclerosis is the most common form of vascular disease and leads to insufficient blood supply to critical body organs, resulting in heart attack, stroke, and kidney failure. Additionally, atherosclerosis causes major complications in those suffering from hypertension and diabetes, as well as tobacco smokers. Atherosclerosis is a form of chronic vascular injury in which some of the normal vascular smooth muscle cells ("VSMC") in the artery wall, which ordinarily control vascular tone regulating blood flow, change their nature and develop "cancer-like" behavior. These VSMC become abnormally proliferative, secreting substances (growth factors, tissue-degradation enzymes and other proteins) which enable them to invade and spread into the inner vessel lining, blocking blood flow and making that vessel abnormally susceptible to being completely blocked by local blood clotting, resulting in the death of the tissue served by that artery.

Restenosis, the recurrence of stenosis or artery stricture after corrective surgery, is an accelerated form of atherosclerosis. Recent evidence has supported a unifying hypothesis of vascular injury in which coronary artery restenosis along with coronary vein graft and cardiac allograft atherosclerosis can be considered to represent a much accelerated form of the same pathogenic process that results in spontaneous atherosclerosis (Ip, J. H., et al., (1990) *J Am Coll Cardiol*, 15:1667–1687; Muller, D. W. M., et al., (1992) *J Am Coll Cardiol*, 19:418–432). Restenosis is due to a complex series of fibroproliferative responses to vascular injury involving potent growth-regulatory molecules, including platelet-derived growth factor (PDGF) and basic fibroblast growth factor (bFGF), also common to the later stages in atherosclerotic lesions, resulting in vascular smooth muscle cell proliferation, migration and neointimal accumulation.

Restenosis occurs after coronary artery bypass surgery (CAB), endarterectomy, and heart transplantation, and particularly after heart balloon angioplasty, atherectomy, laser ablation or endovascular stenting (in each of which one-third of patients redevelop artery-blockage (restenosis) by 6 months), and is responsible for recurrence of symptoms (or death), often requiring repeat revascularization surgery. Despite over a decade of research and significant improvements in the primary success rate of the various medical and surgical treatments of atherosclerotic disease, including angioplasty, bypass grafting and endarterectomy, secondary failure due to late restenosis continues to occur in 30–50% of patients (Ross, R. (1993) *Nature*, 362:801–809).

As a result, a need exists for a successful chemotherapeutic therapy to reduce or prevent artery-blockage. The most effective way to prevent this disease is at the cellular level, as opposed to repeated revascularization surgery which can carry a significant risk of complications or death, consumes time and money, and is inconvenient to the patient.

Microtubules, cellular organelles present in all eukaryotic cells, are required for healthy, normal cellular activities. They are an essential component of the mitotic spindle needed for cell division, and are required for maintaining cell shape and other cellular activities such as motility, anchorage, transport between cellular organelles, extracellular secretary processes (Dustin, P. (1980) *Sci. Am.*, 243: 66–76), as well as modulating the interactions of growth factors with cell surface receptors, and intracellular signal transduction. Furthermore, microtubules play a critical regulatory role in cell replication as both the c-mos oncogene and CDC-2-kinase, which regulate entry into mitosis, bind to and phosphorylate tubulin (Verde, F. et al. (1990) *Nature*, 343:233–238), and both the product of the tumor suppressor gene, p53, and the T-antigen of SV-40 bind tubulin in a ternary complex (Maxwell, S. A. et al. (1991) *Cell Growth Differen.*, 2:115–127). Microtubules are not static, but are in dynamic equilibrium with their soluble protein subunits, the α- and β-tubulin heterodimers. Assembly under physiologic conditions requires guanosine triphosphate (GTP) and certain microtubule associated and organizing proteins as cofactors; on the other hand, high calcium and cold temperature cause depolymerization.

Interference with this normal equilibrium between the microtubule and its subunits would therefore be expected to disrupt cell division and motility, as well as other activities dependent on microtubules. This strategy has been used with significant success in the treatment of certain malignancies. Indeed, antimicrotubule agents such as colchicine and the vinca alkaloids are among the most important anticancer drugs. These antimicrotubule agents, which promote microtubule disassembly, play principal roles in the chemotherapy of most curable neoplasms, including acute lymphocytic leukemia, Hodgkin's and non-Hodgkin's Lymphomas, and germ cell tumors, as well as in the palliative treatment of many other cancers.

The newest and most promising antimicrotubule agent under research is taxol. Taxol is an antimicrotubule agent isolated from the stem bark of *Taxus brevifolia*, the western (Pacific) yew tree. Unlike other antimicrotubules such as colchicine and the vinca alkaloids which promote microtubule disassembly, taxol acts by promoting the formation of unusually stable microtubules, inhibiting the normal dynamic reorganization of the microtubule network required for mitosis and cell proliferation (Schiff, P. B., et al. (1979) *Nature* 277: 665; Schiff, P. B., et al. (1981) *Biochemistry* 20: 3247). In the presence of taxol, the concentration of tubulin required for polymerization is significantly lowered; microtubule assembly occurs without GTP and at low temperatures, and the microtubules formed are more stable to depolymerization by dilution, calcium, cold, and inhibitory drugs. Taxol will reversibly bind to polymerized tubulin, and other tubulin-binding drugs will still bind to tubulin even in the presence of taxol.

Taxol has one of the broadest spectrum of antineoplastic activity, renewing serious interest in chemotherapeutic strategies directed against microtubules (Rowinsky, E. K., et al. (1990) *Jrnl. of the Nat'l. Cancer Inst.*, 82:1247–1259). In recent studies, taxol has shown significant activity in advanced and refractory ovarian cancer (Einzig, A. I., et al. (1992) *J. Clin. Oncol.*, 10:1748), malignant melanoma (Einzig, A. I. (1991) *Invest. New Drugs*, 9:59–64), as well as in cancers of the breast (Holmes, F. A., et al. (1991) *JNCI*, 83:1797–1805), head and neck, and lung.

Taxol has been studied for its effect in combating tumor growth in several clinical trials using a variety of administration schedules. Severe allergic reactions have been observed following administration of taxol. However, it is has been demonstrated that the incidence and severity of allergic reactions is affected by the dosage and rate of taxol infusion (Weiss, R. B., et al. (1990) *J. Clin. Oncol.* 8: 1263).

Cardiac arrhythmias are associated with taxol administration, and like allergic reactions, their incidence is affected by the dosage and rate of taxol administration. Sinus bradycardia and Mobitz II arrhythmia will develop in approximately 40% and 5% of patients, respectively, beginning 4–6 hours after the start of a taxol infusion, and continuing for 4–8 hours after its completion. In most patients, the abnormal rhythm is transient, asymptomatic, hemodynamically stable, and does not require cardiac medications or electrical pacing. Additionally, it has been observed that the incidence of severe cardiac events is low in patients receiving taxol alone. Thus, infusion times up to 24 hours have been used in treatment with taxol to decrease the incidence of toxicity and allergic reaction to the drug.

During angioplasty, intaarterial balloon catheter inflation results in deendothelialization, disruption of the internal elastic lamina, and injury to medial smooth muscle cells. While restenosis likely results from the interdependent actions of the ensuing inflammation, thrombosis, and smooth muscle cell accumulation (Ferrell, M., et al. (1992) *Circ.*, 85:1630–1631), the final common pathway evolves as a result of medial VSMC dedifferentiation from a contractile to a secretory phenotype. This involves, principally, VSMC secretion of matrix metalloproteinases degrading the surrounding basement membrane, proliferation and chemotactic migration into the intima, and secretion of a large extracellular matrix, forming the neointimal fibropoliferative lesion. Much of the VSMC phenotypic dedifferentiation after arterial injury mimics that of neoplastic cells (i.e., abnormal proliferation, growth-regulatory molecule and protease secretion, migration and basement invasion).

Although others have investigated the use of the antimicrotubule agent colchicine in preventing restenosis, opposite conclusions have been reported (See Currier, et al., "Colchicine Inhibits Restenosis After Iliac Angioplasty In The Atherosclerotic Rabbit" (1989) *Circ.*, 80:II-66; O'Keefe, et al., "Ineffectiveness Of Colchicine For The Prevention Of Restenosis After Coronary Angioplasty" (1992) *J. Am. Coll. Cardiol.*, 19:1597–1600). The art fails to suggest the use of a microtubule stabilizing agent such as taxol in preventing or reducing this disease. Thus, the method of the present invention is to prevent or reduce the development of atherosclerosis or restenosis using a microtubule stabilizing agent such as taxol or a water soluble taxol derivative. This microtubule stabilizing mechanism of atherosclerosis or restenosis prevention is supported by the analogous results in experiments on cellular proliferation and migration using taxol and $^2H_2O$ (deuterium oxide), which exert comparable microtubule effects via different underlying mechanisms.

Accordingly, an object of this invention is to provide a method to reduce or prevent the development of atherosclerosis or restenosis using treatment with a drug which promotes highly stabilized tubule formation.

An additional object of this invention is to provide a method of preventing or reducing atherosclerosis or restenosis using a pharmaceutical preparation containing a low dosage of taxol or water soluble taxol derivative.

All references cited are herein incorporated by reference.

SUMMARY OF THE INVENTION

In accordance with these and other objects of the present invention, a method of preventing or reducing atherosclerosis or restenosis is provided, which comprises treatment with a therapeutically effective amount of a microtubule stabilizing agent such as taxol or a water soluble taxol derivative. A therapeutically effective amount of agent is an amount sufficient to prevent or reduce the development of atherosclerosis or restenosis.

This method provides an effective way of preventing or reducing the development of atherosclerosis or restenosis in those patients susceptible to such disease. Additionally, because of the low dose of chemotherapeutic agent used, the chance of a patient developing adverse reactions is potentially reduced.

DETAILED DESCRIPTION OF THE INVENTION

Figure 1:
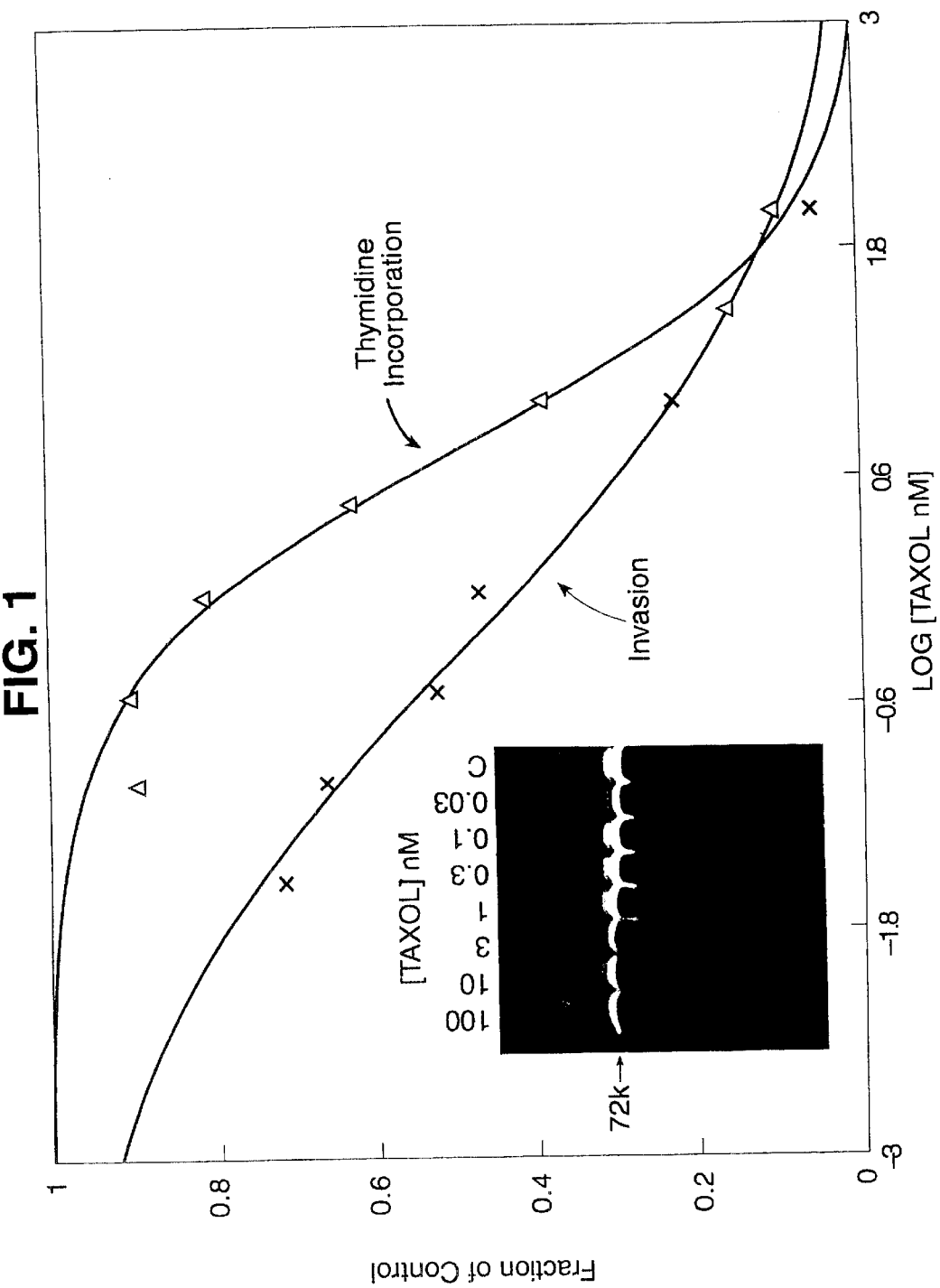
FIG. 1 depicts the taxol induced impairment of the ability of VSMC to invade filters coated with basement membrane proteins, and taxol inhibition of cultured VSMC [$^3$H]-thymidine incorporation.

The practice of an embodiment in the present invention may be accomplished via several alternative drug delivery routes, such as intraperitoneal or subcutaneous injection, continuous intravenous infusion, oral ingestion or local (direct) delivery, or a combination of two or more. When formulating a solution for injection or continuous infusion, one must first prepare a taxol solution. Taxol is supplied through CTEP, DCT, NCI (IND#22850) as a concentrated solution, 6 mg/ml, in 5 ml vials (30 mg/vial) in a polyoxyethylated castor oil (Cremophor EL®) 50% and dehydrated alcohol, USP (50%) vehicle. The intact vials should be stored under refrigeration and diluted prior to use. When diluted in either 5% Dextrose Injection or 0.9% Sodium Chloride, taxol concentrations of 0.3–1.2 mg/ml are physically and chemically stable for at least 12 hours at room temperature. (NCI Investigation Drugs; Pharmaceutical Data (1990)). It has also been demonstrated that taxol concentrations of 0.6 mg/ml diluted in either D5W or NS and 1.2 mg/ml diluted in NS prepared in polyolefin containers are stable for at least 25 hours at ambient temperatures (20–23° C). (Waugh, et al. (1990) *Am. J. Hosp. Pharm.* 48, 1520). Although these concentrations have exhibited stability for the above periods of time, they are not meant to limit the practice of the present invention wherein any concentration of taxol may be utilized.

All solutions of taxol exhibit a slight haziness directly proportional to the concentrations of drug and time elapsed after preparation. Formulation of a small number of fibers in the solution (within acceptable limits established by the USP Particulate Matter Test for LVP's) has been observed after preparation of taxol infusion solutions. While particulate formation does not indicate loss of drug potency, solutions exhibiting excessive particulate matter formation should not be used. Therefore, when administering via continuous infusion, in-line filtration may be necessary and can be accomplished by incorporating a hydrophilic, microporous filter with a pore size no greater than 0.22 microns (IVEX-HP In Line Filter Set-SL, 15", Abbott model # 4525 or equivalent) into the fluid pathway distal to an infusion pump.

Taxol must be prepared in non-plasticized solution containers (e.g., glass, polyolefin, or polypropylene) due to leaching of diethylhexylphthlalate (DEHP) plasticizer from polyvinyl chloride (PVC) bags and intravenous tubing. Taxol must not be administered through PVC intravenous or injection sets. Therefore, polyolefin- or polyethylene-line sets, such as IV nitroglycerin sets (or equivalent) should be used to connect the bottle or bag (containing the taxol solution for a continuous infusion) to the IV pump, a 0.22 micron filter is then attached to the IV set, and then may be directly attached to the patient's central access device. If necessary, a polyolefin-line extension set (Polyfin™ Extension Set, MiniMed Technologies, Model #126) can be used to provide additional distance between the IV pump and the patient's central access device.

One category of taxol use would encompass the prevention of recurrent stenosis (restenosis) post therapeutic coronary- or peripheral-artery angioplasty or atherectomy, after coronary bypass graft or stent surgery, or after peripheral vascular surgery (e.g., carotid or other peripheral vessel endarterectomy, vascular bypass, stent or prosthetic graft procedure). A human dosing schedule can consist of (but not be limited to) 24-hour continuous IV pretreatment with up to about 0.5–2 mg/kg (20–80 mg/m$^2$) prior to the vascular procedure, about 0.25–2 mg/kg (10–80 mg/m$^2$) continuous IV infusion over the 24 hours post-procedure, then about 0.25–2 mg/kg (10–80 mg/m$^2$) continuous IV infusion over 24 hours every 21 days for 1 to 6 cycles. Such a dosage is significantly lower than that used to treat human cancers (approximately 4–6 mg/kg).

Another category of taxol use would encompass the primary prevention, or the attenuation, of vascular disease (atherosclerosis) development. Certain of these applications (examples of which include the prevention of cardiac allograft (transplant) atherosclerosis, the multi-organ system failure resulting from the vascular complications of diabetes mellitus or accelerated, medically-refractory atherosclerosis in patients who are poor surgical candidates) may require the later treatment cycles to be continuous low-dose (1–5 mg/m$^2$/day) IV infusions over 5–7 days. Each of the taxol treatments will generally require pretreatment with dexamethasone 20 mg orally 14 and 7 hours prior to taxol, diphenhydramine 50 mg IV and cimetidine 300 mg IV 30 min prior to taxol, to minimize potential episodes of allergic reaction. Additional applications that may not be associated with a surgical procedure include treatment of vascular fibromuscular dysplasia, polyarteritis nodosa, and Takayasu's arteritis. Each of the aforementioned applications may also be amenable to selective,. localized application of sustained-release preparations of taxol (or other microtubule-stabilizing agent) which would enable high dosage local drug delivery with little systemic toxicity.

Additionally, water soluble derivatives of taxol can also be used in the present invention. The water soluble derivatives of taxol, as described in U.S. Pat. No. 5,157,049 to Haugwitz, et al. (incorporated herein by reference) include, but are not limited to, 2'-succinyl-taxol; 2'-succinyl-taxol triethanolamine; 2'-glutaryl-taxol; 2'-glutaryl-taxol triethanolamine salt; 2'-O-ester with N-(dimethylaminoethyl) glutamide; 2'-O-ester with N-(diethylaminoethyl) glutamide hydrochloride salt. These water soluble taxol derivatives can be administered in a dosage schedule analogous to that given above for taxol with the appropriate modifications pending clarification of the pharmacokinetics of these agents.

A pharmaceutical composition comprising an effective amount of water soluble derivative of taxol as an active ingredient is easily prepared by standard procedures well known in the art, with pharmaceutically acceptable non-toxic sterile carriers, if necessary. Such preparations could be administered orally or in injectable form, or directly to an affected area, to a patient at risk of developing or suffering from atherosclerosis to prevent or reduce the development of the disease.

The following examples illustrate the effectiveness of taxol (or other microtubule-stabilizing agents including, but not limited to, water soluble derivatives of taxol) in inhibiting the proliferation and migration of vascular smooth muscle cells, and should not be used to limit the scope of the present invention.

EXAMPLE 1

The in vitro ability of cultured VSMCs, pretreated with different taxol concentrations, to invade filters coated with reconstituted basement membrane proteins was tested to evaluate how taxol-induced microtubule bundling would impair cell processes necessary for in vivo neointimal formation.

Vascular Smooth Muscle Cells (VSMCs) were isolated by collagenase/elastase enzymatic digestion of the medial layers of the rat aorta obtained from 6 month old Wistar rats. The cells were maintained in culture with 10% fetal calf serum, high glucose DMEM, and amino acid supplement. Cell cultures were maintained at 37° C. in 5% $CO_2$.

After 18-hour taxol pre-treatment in culture, cells were fixed in 3.7% formalin, permeabilized with 1% Triton X-100, and polymerized tubulin was labelled with mouse anti-β-tubulin antibody (SMI 62 monoclonal antibody to polymerized β-tubulin, Paragon Biotec, Inc., Baltimore, Md.). Secondary labelling was achieved with silver-enhanced, 1 nm gold-conjugated rabbit anti-mouse antibody (Goldmark Biologicals, Phillipsburg, N.J.). Representative light photomicrographs from (A) control, (B) 0.1 nM taxol, (C) 1 nM taxol, and (D) 10 nM taxol treated VSMCs are shown in FIG. 4.

Chemonivasion (Boyden chamber) assays were performed using modified Boyden chamber (Albini, et al.

(1987) *Cancer Res.*, 47:3239–3245), comprising an upper chamber separated from a lower chamber by a porous PVPF filter. PVPF filters (8 μm pore diameter, Nucleopore Filters, Pleasonton, Calif.) were coated and air dried consecutively with solutions containing 100 μg/ml type I collagen, 5 μg/ml fibronectin, and 5 μg reconstituted basement membrane (produced from the Englebreth-Holm-Swarm tumor (Kleinman, et al. (1986) *Biochemistry*, 25:312–318), producing a continuous 10 μm thick coating of matrix material. Boyden chambers were assembled by adding 10 ng/ml PDGF BB in DMEM to the lower (chemoattractant) chamber. Cells (approximately 200,000) suspended in DMEM containing 0.1% BSA were then added to the upper chamber. Some of the cells used in this assays were pretreated 18 hours with taxol (concentration 30 pM to 100 nM) in culture. In the taxol-treated groups, taxol was added to the upper and lower chambers at the same concentration as that used for pretreatment. The chambers were then incubated for 4 hours at 37° C. in a 5% $CO_2$ atmosphere. At the end of the incubation period, the cells were fixed and stained with hematoxylin and eosin. The cells on the upper surface (non-invaders) were mechanically removed and the cells on the underside of the filter (invaders) were counted under 400× magnification (four random fields were counted per filter and all experiments were run in triplicate, and each triplicate assay was repeated at least three times on separate occasions using different VSMC preparations). Chemotaxis was assayed in analogous fashion in the Boyden chambers described above, except that the reconstituted basement membrane was omitted. This chemoinvasion assay is accepted by those skilled in the art as exhibiting high correlation between invasiveness in vitro and cellular behavior as it occurs in vivo (Iwamoto, Y., et al. (1992) *Advances In Experimental Medicine & Biology*, 324:141–9).

Using the PDGF-BB as an attractant, taxol inhibited VSMC invasion with half-maximal inhibitory concentration of 0.5 nM. Taxol caused essentially complete inhibition at 100 nM, and significant inhibition was still resolvable at 30 pM (the lowest dose used)(FIG. 1). A chemotaxis assay (filter coated only with fibronectin and collagen I, without basement membrane proteins occluding the filter pores) with PDGF-BB as the attractant was performed in analogous fashion, yielding the identical outcome. These results demonstrate that taxol, at least at nanomolar drug levels, inhibits VSMC invasion primarily via inhibition of locomotion and/or shape changes, rather than by inhibiting cellular secretion of collagenases and metalloproteinases, which are known to be necessary for VSMC to penetrate basement membrane proteins in this assay.

Gelatinase zymography was performed on the supernatants removed after the 4 hour conclusion of the Boyden assays described above. Gelatin-degrading proteinases secreted into the media by VSMCs were analyzed by non-reducing sodium dodecyl sulfate-polyacrylamide gel electrophoresis in 10% polyacrylamide gels containing 0.1% (w/v) gelatin. Following electrophoresis, the gelatinases were renatured by incubating the gel for 30 min. at 23° C. in 2.5% (v/v) Triton X-100 followed by 18 hour incubation at 37° C. in 0.2 M NaCl, 5 mM $CaCl_2$ 0.02% Brij 35 (w/v), 50 mM Tris-HCl (pH 7.6). The gels were stained for 90 minutes with 0.5% Coomassie Brilliant Blue G-250 and destained with 10% acetic acid, 40% methanol. Gelatinolytic activity was indicated by a clear band against the background of blue-stained gelatin.

Figure 2A:
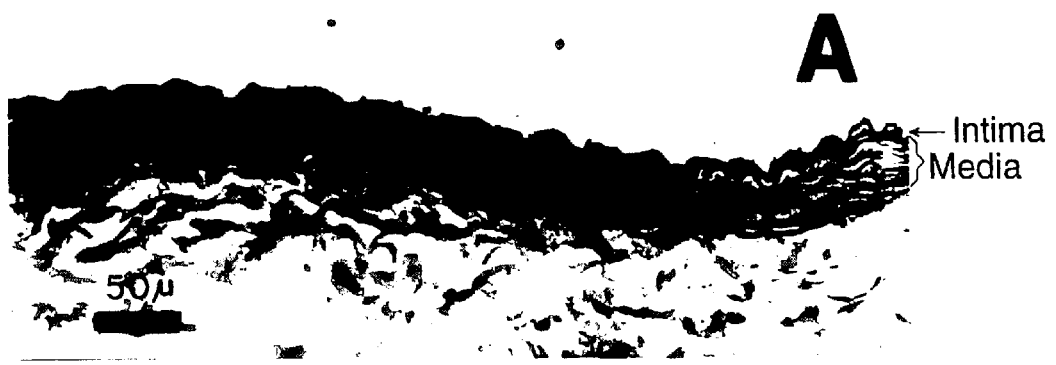
FIG. 2 shows taxol inhibition of smooth muscle cell neointimal accumulation after balloon catheter injury of the rat carotid artery.
Figure 2B:
Figure 2C:

These gelatinase zymography assays from the Boyden chamber invasion experiments confirm that the level of VSMC collagenase secretion did not vary significantly over the taxol range 30 pM to 100 nM, compared to control (FIG. 2, inset).

EXAMPLE 2

To confirm the fact that microtubule stabilization and hyperpolymerization is the critical and sufficient factor involved in taxol-inhibition of VSMC invasiveness, the chemoinvasion (Boyden chamber) assay was run with deuterium oxide ($^2H_2O$ heavy water). Deuterium oxide enhances microtubule/tubulin polymerization via a mechanism distinct from that of taxol. A combination of the isotope and solvent effects of deuterium oxide reversibly increases microtubule polymerization both by reducing the critical concentration for polymerization for αβ-tubulin heterodimers via enhanced tubulin hydrophobic interactions (Itoh, T. J., et al. (1984) *Biochim. Biophys. Acta.*, 800:21–27), and by converting a population of unpolymerizable tubulin to the polymerizable form (Takahashi, T. C., et al. (1984) Cell Struct. Funct., 9:45–52).

VSMC's were isolated by collagense/elastase enzymatic digestion of the medial layers of the rat aorta obtained from 6 month old Wistar rats. The cells were maintained in culture with 10 % fetal calf serum, high glucose DMEM, and amino acid supplement. Cell cultures were maintained at 37° C. in 5% $CO_2$.

Figure 5B:
FIG. 5 shows deuterium oxide induced microtubule bundling in cultured VSCM's.
Figure 5A:

In deuterium oxide-treated cells, $^2H_2O$ (v/v) was substituted for water ($H_2O$) in the preparation of the DMEM from concentrated stock. After 18-hour deuterium oxide pretreatment in culture, cells were fixed in 3.7% formalin, permeabilized with 1% Triton X-100, and polymerized tubulin was labelled with mouse anti-β-tubulin antibody (SMI 62 monoclonal antibody to polymerized β-tubulin, Paragon Biotec, Inc., Baltimore, Md.). Secondary labelling was achieved with silver-enhanced, 1 nm gold-conjugated rabbit anti-mouse antibody (Goldmark Biologicals, Phillipsburg, N.J.). Representative light photomicrographs from (A) control, and (3) 75 % deuterium oxide treated VSMCs are shown in FIG. 5.

Chemoinvasion assays were performed using a modified Boyden chamber, consisting of an upper chamber separated from a lower chamber by a porous PVPF filter. PVPF filters (8 μm pore diameter, Nucleopore Filters, Pleasonton, Calif.) were coated and air dried consecutively with solutions containing 100 μg/ml type I collagen, 5 μg/ml fibronectin, and 5 μg reconstituted basement membrane (produced from the Englebreth-Holm-Swarm tumor), producing a continuous 10 μm thick coating of matrix material. Boyden chambers were assembled with PDGF-BB 10 ng/ml in DMEM in the lower (chemoattractant) chamber, then cells (approximately 200,000) suspended in DMEM containing 0.1% BSA were added to the upper chamber. Some of the cells used in these assays were pretreated 18 hours with deuterium oxide (25%, 50%, or 75 % v/v substitution for $H_2O$) in culture. In the deuterium oxide-treated groups, $^2H_2O$ substituted DMEM (v/v) was added to the upper and lower chambers at the same concentration as that used for pretreatment. The chambers were then incubated for 4 hours at 37° C. in a humidified 5% $CO_2$ atmosphere. At the conclusion of the experiment, the filters were removed and the cells were fixed and stained with hematoxylin and eosin. After the cells on the upper surface of the filter (non-invaders) were mechanically removed, the cells on the underside (invaders) were counted under 400× magnification (four random fields were counted per filter and all experiments were run in triplicate).

Pretreating cultured VSMCs for 18 hours with 25%, 50% or 75% deuterium oxide caused dose-dependent microtubule hyperpolymetization similar to that observed with taxol.

Figure 3:
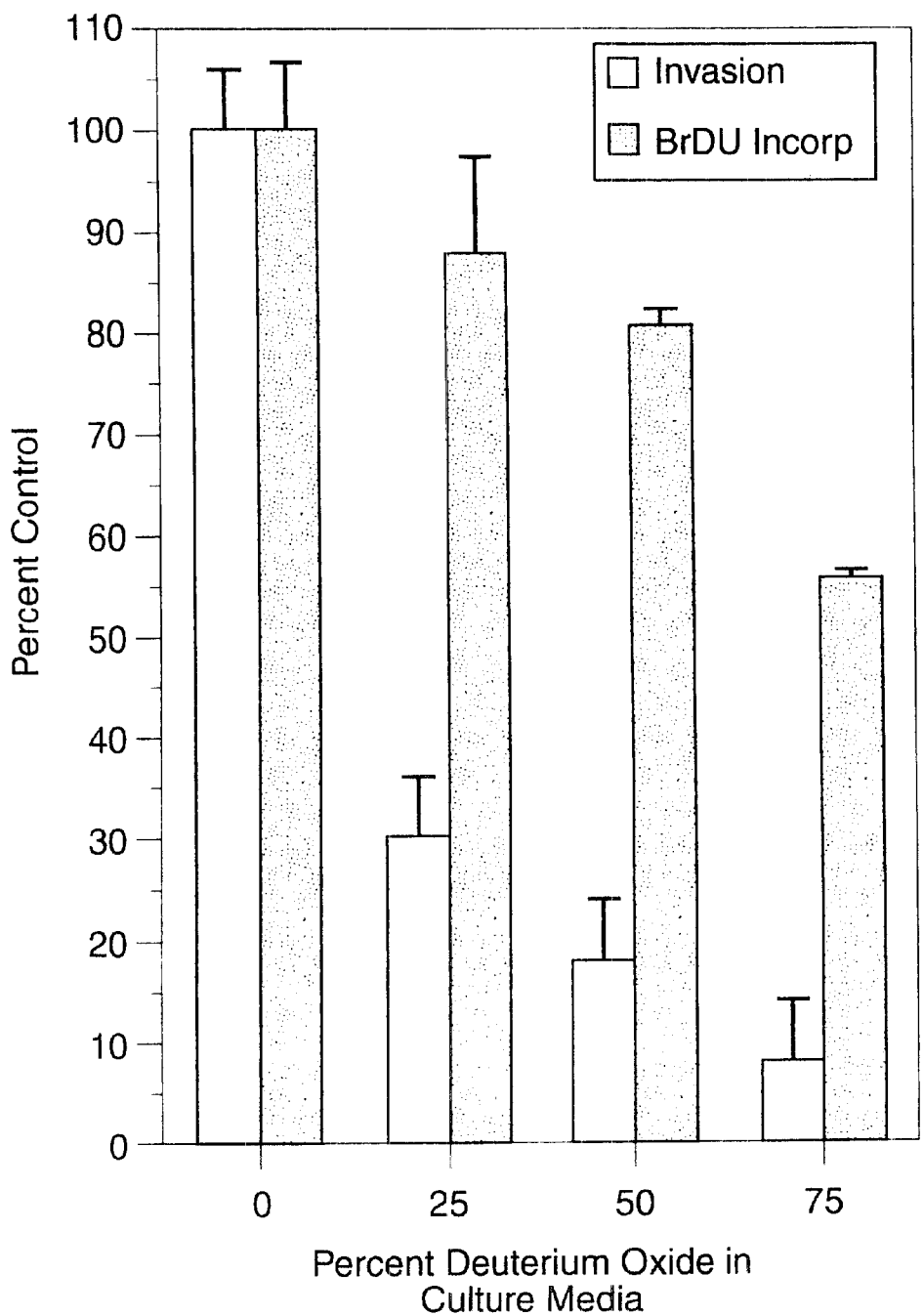
FIG. 3 depicts deuterium oxide dose-dependent inhibition of VSMC chemoinvasion, and deuterium oxide inhibition of cultured VSMC bromodeoxyuridine (BrDU) incorporation.
Figure 4A:
FIG. 4 shows concentrations of taxol caused dose-dependent microtubule bundling in VSMC's cultured on plastic.
Figure 4B:
Figure 4C:
Figure 4D:
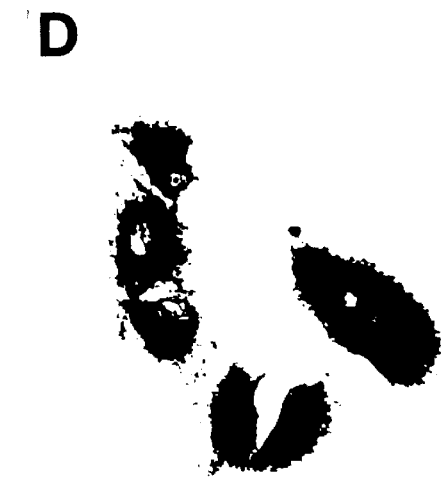

This treatment likewise inhibited PDGF-mediated VSMC Boyden chamber invasion in a dose-dependent fashion, achieving half-maximal inhibition at 25% $^2H_2O$, and nearly complete inhibition at 75% $^2H_2O$ (FIG. 3).

EXAMPLE 3

In addition to cell recruitment and migration, the various growth regulatory molecules elaborated after arterial injury, such as PDGF and bFGF, are also implicated in mitogenesis and cellular proliferation. To measure the effect of taxol on VSMC DNA synthesis, [$^3H$]thymidine incorporation was measured. VSMCs were plated at $4.5 \times 10^4$ on 24-well plates. Following 5 hr. incubation in 10% FCS+DMEM, 0.5 mCi [$^3H$]thymidine was added and the incubation continued for an additional 16 hrs. Cells were washed twice with phosphate-buffered saline, extracted with 10% TCA for 2 hrs. on ice, then centrifuged at 2,000 g for 10 mins. Supernatants were decanted and pellets were solubilized in 0.5 ml of 1 N NaOH. After neutralizing with 0.5 ml of 1 N HCl, [$^3H$]thymidine uptake was determined by a Beckman liquid scintillation counter. VSMCs were treated with the various concentrations of taxol for both the 18 hr. prior to the addition of the thymidine and during thymidine incorporation. Each condition of these experiments was performed in triplicate.

Taxol inhibited cultured VSMC [$^3H$]thymidine incorporation, an index of cell division, in a dose-dependent fashion, with a half-maximal inhibitory concentration of 5 nM. Taxol caused essentially complete inhibition at 100 nM, and significant inhibition was resolvable at 1 nM (FIG. 1). That this inhibitory profile differs somewhat from that of invasion and chemotaxis, demonstrating one log-concentration-unit lower sensitivity but with steeper concentration-dependence, likely arises because of the considerably different roles played by mircotubules between these processes. Taxol also inhibited PDGF-BB-stimulated cfos mRNA expression in this cultured VSMC model, in a dose-dependent fashion, with a half-maximal inhibitory concentration of 1 nM, with essentially complete inhibition above 20 nM. Thus, inhibition of immediate early gene induction is another important mechanism by which taxol blocks growth factor stimulation in VSMCs, and may underlie, at least in part, the thymidine incorporation results.

Thus, taxol significantly inhibits cultured VSMC in vitro invasion and proliferation through interference with microtubule function, disrupting locomotion and the ability to alter shape, as well as growth-factor stimulated early gene expression and cell proliferation, at concentrations one hundred- to one thousand-fold lower than used to treat human cancer.

EXAMPLE 4

Incorporation of the thymidine analog, bromodeoxyuridine (BrDU) was measured to determine the effect of deuterium oxide on VSMC DNA synthesis. VSMCs were plated at $4.5 \times 10^4$ on 24-well plates. Following 20 hr incubation in 10% FCS+DMEM at various $^2H_2O$ concentrations, 10 $\mu$M BrDU was added and the incubation continued for an additional 4 hr. Cells were washed twice with phosphate-buffered saline (PBS) and fixed with 100% methanol ($-20°$ C.) for 10 minutes. The cells were incubated for 2 hr with 1N HCl to denature the DNA, and subsequently washed 4 times in PBS. Mouse monoclonal BrDU antibody (Boehringer Mannheim) in 2% BSA-PBS was incubated with cells for 1 hr. After PBS wash, goat anti-mouse antibody conjugated with alkaline phosphatase was added. Cell nuclei containing BrDU substituted for thymidine stained red with alkaline phosphatase substrate, while all other nuclei stained blue. The fraction of BrDU-positive nuclei was compared between control (defined as 100%) and that of the deuterium oxide-pretreated groups.

The results indicated that deuterium oxide, similar to taxol, inhibited cultured VSMC proliferation and DNA synthesis in a dose-dependent fashion, consistent with the critical balance of microtubule-tubulin dynamics in VSMC proliferation.

While taxol and deuterium oxide potentially have multiple intracellular effects, the coincidence of their parallel effects on microtubules (despite different mechanisms of action) and on VSMC functionality at multiple levels, indicates that the common microtubule stabilizing mechanism of action is responsible for the observed functional changes. Thus, based on the results of experiments with both taxol and deuterium oxide, it is evident that microtubules are involved in the control of the most critical and sensitive intracellular mechanisms necessary for VSMCs to undergo the multiple transformations involved in the development of atherosclerosis and restenosis after arterial injury, making microtubules particularly strategic targets to influence the outcome.

EXAMPLE 5

Under a protocol approved by the National Institute on Aging Animal Care and use Committee, 6 month Wistar rats from the GRC colony were anesthetized with 20 mg/kg body weight pentobarbital, 2 mg/kg body weight ketamine, and 4 mg/kg body weight xylazine intraperitoneally. The left external carotid artery was cannulated with 2-French Fogarty embolectomy catheter, inflated with saline and passed three times up and down the common carotid artery to produce a distending, deendothelializing injury. The animals were treated with 2 mg/kg body weight taxol solution or the control animals with vehicle alone (13.4 ml/kg body weight per day of 1:2:2:165 DMSO:Cremophor EL:Dehydrated ethanol:phosphate buffered saline) by intraperitoneal injection beginning 2 hours after injury. The taxol solution or vehicle alone was administered once daily, as an intraperitoneal injection, for the next 4 days. After 11 days the animals (8 taxol-treated and 10 vehicle-treated) were anesthetized as above and the carotid artery was isolated and fixed in 10% buffered formalin and embedded in paraffin. Cross sections of the carotids were mounted on microscope slides and stained with hematoxylin and eosin stain. The image of the carotid artery was projected onto a digitizing board and the cross sectional areas of the intima and the media were measured. The results are shown in FIG. 2. As indicated in the prior art (Ferns, G. A. A. et al. (1991) *Science*, 253:1129–1132) the rat carotid artery injury model of restenosis can be useful in the study of human restenosis, and indicate potential therapeutic action in humans.

Quantitative analysis of injured carotid segments showed that taxol treatment reduced the neointimal area by 70% compared to vehicle treated animals (Table I) (▲P<0.001; †P=NS; ‡P<0.001). Several of the taxol-treated animals showed virtually no discernable nbointima (in the presence of denuded endothelium, proving injury), while all vehicle treated animals demonstrated at least modest neointimal thickening.

While the in vivo systemic taxol dose used in these experiments (2 mg/kg) is significantly lower than that ordinarily used to treat human cancers (approximately 3–6 mg/kg), dramatically lower systemic dosing with sustained or even improved efficacy could be possible combining a pretreatment regimen with the optimal treatment duration. Furthermore, since the goal of therapy is to keep the "activated" VSMCs in check, or preferably to prevent activation in the first place, until the stimulus for growth and migration has resolved (rather than causing cytotoxicity resulting in cell death), the goal of short-term therapy with limited toxicity may be possible in humans. Ultimately, local sustained-release delivery systems may offer the best solution to prevent restenosis post-angioplasty, enabling high local concentrations of drug delivery and essentially eliminating problems of systemic toxicity. Drug delivery systems that can be valuable include drug-impregnated polymer-coated metallic stents, biodegradable drug-eluting polymer stents, and genetically primed endothelial cells to coat metallic stents or be delivered directly as a local endothelial cell covering. (Muller, D. W. M. et al. (1991) *JACC* 17:126b–131b). These systems allow safe use of a chemotherapeutic agent without systemic side effects. Alternatively, treatment may involve a period of pretreatment (i.e., before vascular surgery) via continuous intravenous infusion for a period of time, followed by a different therapy during (local, direct delivery) or after (oral, injection) surgery.

The above examples teach taxol's (or other microtubule-stabilizing agent including, but not limited to, water soluble derivatives of taxol) potential beneficial uses to prevent artery blockage and thereby reduce the possibility of, or prevent, heart attacks, strokes, kidney failure and renal dialysis, blindness, limb amputations, nerve loss, need for corrective vascular surgery/angioplasty or organ transplantation, and premature and permanent disability requiring chronic hospitalization. The invention has been described in detail, but it will be understood that the invention is capable of other different embodiments. As is readily apparent to those skilled in the art, variations and modifications can be affected within the spirit and scope of the invention. Accordingly, the foregoing disclosure and description are for illustrative purposes only, and do not in any way limit the invention, which is defined only by the claims.

TABLE 1

| Group | Intima (mm$^2$) | Media (mm$^2$) | I/M |
|---|---|---|---|
| Vehicle | 0.09 ± 0.01 | 0.14 ± 0.01 | 0.66 ± .08 |
| Taxol | 0.03 ± 0.01* | 0.16 ± 0.02† | 0.18 ± .04‡ |

We claim:

1. A method of inhibiting or reducing restenosis or atherosclerosis in a patient comprising:

treating the patient with at least one anti-allergic agent for taxol or a taxol derivative; and subsequently systemically delivering a pharmaceutical preparation comprising a therapeutically effective amount of taxol or a taxol derivative, wherein the systemic delivery is selected from intravenous or oral.

2. The method of claim 1, wherein the systemic delivery comprises more than one treatment cycle.

3. The method of claim 1, wherein the taxol or taxol derivative is administered at a dose lower than a dose used to treat human cancers.

4. The method of claim 1, wherein the anti-allergic agent is selected from dexamethasone and diphenhydramine.

* * * * *